United States Patent
Vaidyanathan et al.

(10) Patent No.: US 6,271,219 B2
(45) Date of Patent: Aug. 7, 2001

(54) TOPICAL FORMULATIONS COMPRISING SKIN PENETRATION AGENTS AND THE USE THEREOF

(76) Inventors: Rajaram Vaidyanathan, 44 Santa Clara, San Clemente, CA (US) 92672; Phuong M. Vo, 20 Appomattox Ave., Irvine, CA (US) 92620; George N. Manning, 111 San Lucas Ave., Moss Beach, CA (US) 94038; Donald J. Gerhart, 2709 Buckboard Dr., Hillsborough, NC (US) 27278; Atef A. Helmy, 2572 W. Runyon Pl., Anaheim, CA (US) 92804; Geoffrey Allan, 5408 Cary Street Rd., Richmond, VA (US) 23226

( * ) Notice: Subject to any disclaimer, the term of this patent is extended or adjusted under 35 U.S.C. 154(b) by 0 days.

(21) Appl. No.: 09/406,918

(22) Filed: Sep. 28, 1999

Related U.S. Application Data

(60) Provisional application No. 60/140,756, filed on Jun. 25, 1999.

(51) Int. Cl.[7] .................................................. A61K 31/56
(52) U.S. Cl. ........................ 514/174; 514/947; 514/861; 514/863
(58) Field of Search ................................... 514/181, 739, 514/863, 861, 864, 946, 947

(56) References Cited

U.S. PATENT DOCUMENTS

| | | | |
|---|---|---|---|
| 4,122,170 | 10/1978 | Rajadhyaksha | 424/180 |
| 4,316,893 | 2/1982 | Rajadhyaksha | 424/180 |
| 4,444,762 | 4/1984 | Rajadhyaksha | 424/180 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,863,970 | * 9/1989 | Patel et al. | 514/784 |
| 4,886,783 | 12/1989 | Minaskanian et al. | 574/29 |
| 5,391,548 | * 2/1995 | Francoeur et al. | 514/213 |
| 5,607,691 | * 3/1997 | Hale et al. | 424/449 |
| 5,834,010 | 11/1998 | Quan et al. | 424/448 |
| 5,952,000 | * 9/1999 | Venkateshwaran et al. | 424/448 |

OTHER PUBLICATIONS

U.S. Trademark Application No. 767,515 filed Dec. 5, 1988.

\* cited by examiner

*Primary Examiner*—William R. A. Jarvis
*Assistant Examiner*—Vickie Kim
(74) *Attorney, Agent, or Firm*—Sterne, Kessler, Goldstein & Fox, P.L.L.C.

(57) ABSTRACT

Disclosed are topical pharmaceutical compositions comprising a pharmaceutically active agent such as a corticosteroid, a diol, cetyl alcohol, glyceryl monostearate, laurocapram, stearyl alcohol, sodium lauryl sulfate and water. Also disclosed is a method for the manufacture of the compositions and methods for treating inflammatory skin conditions with the compositions.

18 Claims, No Drawings

TOPICAL FORMULATIONS COMPRISING SKIN PENETRATION AGENTS AND THE USE THEREOF

CROSS-REFERENCE TO RELATED APPLICATIONS

This application claims the benefit of U.S. Provisional Application No. 60/140,756, filed Jun. 25, 1999.

BACKGROUND OF THE INVENTION

1. Field of the Invention

The present invention relates to topical pharmaceutical compositions comprising a pharmaceutically active agent, laurocapram, and one or more diols, particularly propylene glycol. The invention further relates to the use of the topical pharmaceutical compositions.

2. Related Art

A number of patents disclose compounds which enhance the penetration of physiologically active agents through the skin. See U.S. Pat. Nos. 4,122,170, 4,316,893, 4,444,762, 4,886,783, and 5,834,010.

U.S. Pat. No. 4,552,872 discloses topical pharmaceutical compositions comprising a pharmaceutically active corticosteroid together with a penetration enhancing vehicle containing a $C_3$–$C_4$ diol, and a cell-envelope disordering compound such as oleic acid. The vehicle is substantially free of saturated, straight chain $C_{16}$–$C_{20}$ alcohols and $C_4$–$C_{20}$ mono- or dicarboxylic acids.

U.S. Pat. No. 4,557,934 discloses topical pharmaceutical compositions containing a pharmaceutically active agent, the penetrating enhancing agent 1-dodecylazacycloheptan-2-one (laurocapram), in combination with certain $C_3$–$C_4$ diols. A preferred diol is propylene glycol. Preferred pharmaceutically active agents include corticosteroids such as triamcinolone acetonide, vitamins, antifungal agents, blood calcium regulators, etc.

U.S. Pat. Nos. 4,552,872, and 4,557,934 also teach that certain straight chain, saturated $C_{16}$–$C_{20}$ normal fatty alcohols may interfere with penetration of the pharmaceutically active agents in the diol formulations, particularly, the propylene glycol formulations, and should be avoided if such interference is too great. In particular, the patents teach that cetyl ($C_{16}$) and stearyl ($C_{18}$) n-alcohols are capable of significant interference with the penetration enhancement of the formulation. In a preferred embodiment, the compositions are substantially free of such compounds and preferably contain less than 0.5% of cetyl or stearyl alcohol. Example 9 of the '934 patent shows that the skin penetration of the pharmaceutically active agent triamcinolone acetonide from a propylene glycol vehicle is reduced 39% upon the addition of cetyl alcohol at a concentration of 3% by weight.

Surprisingly, it has now been discovered that topical formulations comprising significant amounts of a pharmaceutically active agent such as a corticosteroid, cetyl alcohol, stearyl alcohol, laurocapram and a diol, preferably propylene glycol, are very effective in treating dermatological conditions.

SUMMARY OF THE INVENTION

The invention relates to a pharmaceutical composition for topical administration, comprising:

(a) a safe and pharmaceutically effective amount of a pharmaceutically active agent;

(b) about 15–97% by weight of a diol selected from the group consisting of 1,2-propanediol, 1,2-butanediol, 1,3-butanediol, 2,3-butanediol, and mixtures thereof;

(c) about 0.5–25% by weight of cetyl alcohol, (d) about 0.1–25% by weight of glyceryl monostearate;

(e) about 0.9–5.0% by weight of laurocapram;

(f) about 0.5–25% by weight of stearyl alcohol;

(g) about 0.01–1.0% by weight of sodium lauryl sulfate; and (h) water.

The invention also relates to a process for preparing a topical pharmaceutical composition, comprising:

(a) admixing water, a diol and sodium lauryl sulfate at about 70–80° C. at least until the diol and sodium lauryl sulfate dissolve to give an Aqueous Phase Mixture Part A, wherein said diol is selected from the group consisting of 1,2-propanediol, 1,2-butanediol, 1,3-butanediol, 2,3-butanediol, and mixtures thereof;

(b) admixing laurocapram and a pharmaceutically active agent at about 70–80° C. at least until the agent dissolves to give an Agent/Laurocapram Premix Part B;

(c) admixing glyceryl monostearate, cetyl alcohol and stearyl alcohol at about 70–80° C. until at least the admixture melts;

(d) admixing with said melted admixture said Agent/Laurocapram Premix Part B at about 70–80° C. and mixing at least until thoroughly blended to give an Oil (non-aqueous) Phase Mixture Part C;

(e) emulsifying a mixture of Aqueous Phase Mixture Part A and the Oil (non-aqueous) Phase Mixture Part C at about 70–80° C.; and (f) cooling to room temperature.

The pharmaceutically active agent may be added to the Aqueous Phase in step (a) or to the Oil (non-aqueous) Phase in step (d) depending upon the solubility of the pharmaceutically active agent.

The invention also relates to a pharmaceutical composition obtained by the process of the invention.

The invention also relates to a method of treating an inflammatory skin condition in an animal in need thereof, comprising administering an effective amount of the inventive pharmaceutical composition to said animal, wherein the pharmaceutically active agent in the composition is an anti-inflammatory agent, preferably, a corticosteroid, more preferably, triamcinolone, most preferably, triamcinolone acetonide.

The invention relates in part to the discovery that topical pharmaceutical compositions containing pharmaceutically active agents such as corticosteroids, and substantial amounts of cetyl alcohol and stearyl alcohol are very effective topical therapeutic agents, e.g., for treating dermatological conditions. The pharmaceutical composition of the invention comprising 0.05% triamcinolone acetonide as the pharmaceutically active agent was found to potently induce vasoconstriction, and to provide relief from the inflammatory and pruritic manifestations of corticosteroid-responsive dermatoses. The present invention provides for substantial cost savings due to a reduction in the required level of pharmaceutically active agent, results in a rapid onset of pharmacological effects, and is stable and non-irritating. In addition, preservatives are not required and the inventive compositions have acceptable cosmetic and aesthetic properties.

DETAILED DESCRIPTION OF THE PREFERRED EMBODIMENTS

The invention relates to a pharmaceutical composition for topical administration, comprising:
(a) a safe and pharmaceutically effective amount of a pharmaceutically active agent;
(b) about 15–97% by weight of a diol selected from the group consisting of 1,2-propanediol, 1,2-butanediol, 1,3-butanediol, 2,3-butanediol, and mixtures thereof,
(c) about 0.5–25% by weight of cetyl alcohol;
(d) about 0.1–25% by weight of glyceryl monostearate,
(e) about 0.9–5.0% by weight of laurocapram;
(f) about 0.5–25% by weight of stearyl alcohol;
(g) about 0.01–1.0% by weight of sodium lauryl sulfate, and
(h) water.

The preferred diol is 1,2-propanediol, i.e., propylene glycol. The preferred source of glyceryl monostearate is CERASYNT® SD which is a non-compendial emulsifier available from Van Dyk & Co., Inc., although other self-emulsifying grades of glyceryl monostearate may be employed.

Examples of pharmaceutically active agents useful in the present invention include, without limitation, corticosteroids such as hydroxytriamcinolone, alpha methyl dexamethasone, dexamethasone acetate, betamethasone, beclomethasone dipropionate, betamethasone benzoate, betamethasone dipropionate, betamethasone valerate, clobetasol valerate, clobetasol propionate, desonide, desoxymethasone, dexamethasone, difluorosone diacetate, diflucortolone valerate, fluadrenolone, fluclorolone acetonide, flumethasone pivalate, fluocinolone acetonide, fluocinonide, flucortine butylester, flucortolone, fluprednidine (fluprednylidene) acetate, flurandrenolone, halcinonide, hydrocortisone acetate, hydrocortisone butyrate, hydrocortisone valerate, 11-desoxycortisol, methylprednisolone, triamcinolone, triamcinolone acetonide, triamcinolone diacetate, triamcinolone hexacetonide, cortisone, cortodoxone, flucetonide, fludrocortisone, difluorosone diacetate, fluradrenolene acetonide, medrysone, amcinafel, amcinafide, betamethasone and the balance of its esters, chloroprednisone, clocortelone, clocortelone pivalate, clescinolone, dichlorisone, difluprednate, flucloronide, flunisolide, fluoromethalone, fluperolone, fluprednisolone, hydrocortisone, meprednisone, paramethasone, paramethasone acetate, prednisolone, prednisolone acetate, prednisolone tebutate, prednisone, beclomethasone dipropionate, alclometasone dipropionate and mometasone furoate.

Other pharmaceutically active agents include agents, synthetic and natural, which have a pharmaceutical effect at the surface of the skin and/or in the subcutaneous layers of the skin such as antimicrobials, antivirals, antibiotics, anthelmintics, anti-inflammatory agents, histamine $H_2$-receptor agonists and antagonists, hormones, vitamins, neoplastic agents, immune-response agents, antithrombotics, sulfones, sunscreens, local anesthetics, muscle relaxants, antitussives, blood regulators, anticoagulants, hemostatics, sedatives, analgesics, adrenergics, antispasmodics, bone-active agents, prostaglandins, antipsychotics, anorexigenics, cholinergics, anticholinergics and sulfonamides. The phrase "pharmaceutically active agent" also includes pharmaceuticals used to treat arthritis, thyroid conditions, hypertension, cardiac conditions, depression, hyperlipidemia, ulcers, malaria, cancer and anxiety.

Mixtures of pharmaceutically active agents, particularly any of the above corticosteroids, are also useful in the present invention.

In a preferred embodiment of the invention, the pharmaceutical composition of the present invention has the following composition:

| Ingredients | Percent (% w/w) (about) |
|---|---|
| Pharmaceutically Active Agent | 0.01–10 |
| Diol | 15–97 |
| Cetyl Alcohol | 0.5–25 |
| Glyceryl Monostearate | 0.1–25 |
| Laurocapram | 0.9–5 |
| Stearyl Alcohol | 0.5–25 |
| Sodium Lauryl Sulfate | 0.01–1 |
| Purified Water | QS ad 100% |

In a more preferred embodiment of the invention, the pharmaceutical composition of the present invention has the following composition:

| Ingredients | Percent (% w/w) (about) |
|---|---|
| Corticosteroid | 0.02–5 |
| Diol | 15–25 |
| Cetyl Alcohol, NF | 1–15 |
| Glyceryl Monostearate | 1–10 |
| Laurocapram | 1–3 |
| Stearyl Alcohol, NF | 1–15 |
| Sodium Lauryl Sulfate, NF (Powder) | 0.1 |
| Purified Water, USP | QS ad 100% |

In another preferred embodiment, the corticosteroid is triamcinolone acetonide.

In a most preferred embodiment, the pharmaceutical composition of the present invention has the following composition:

| Ingredients | Percent (% w/w) |
|---|---|
| Triamcinolone Acetonide, USP | 0.05 |
| Propylene Glycol, USP | 15.00 |
| Cetyl Alcohol, NF | 8.00 |
| CERASYNT ® SD (comprising glyceryl monostearate) | 3.50 |
| Laurocapram | 1.60 |
| Stearyl Alcohol, NF | 1.00 |
| Sodium Lauryl Sulfate, NF (Powder) | 0.10 |
| Purified Water, USP | QS ad 100% |

The invention also relates to a process for preparing a topical pharmaceutical composition, comprising
(a) admixing water, a diol and sodium lauryl sulfate at about 70–80° C. at least until the diol and sodium lauryl sulfate dissolve to give an Aqueous Phase Mixture Part A, wherein said diol is selected from the group consisting of 1,2-propanediol, 1,2-butanediol, 1,3-butanediol, 2,3-butanediol, and mixtures thereof;

(b) admixing laurocapram and a pharmaceutically active agent at about 70–80° C. at least until the agent dissolves to give an Agent/Laurocapram Premix Part B;

(c) admixing glyceryl monostearate, cetyl alcohol and stearyl alcohol at about 70–80° C. until at least the admixture melts;

(d) admixing with said melted admixture said Agent/Laurocapram Premix Part B at about 70–80° C. and mixing at least until thoroughly blended to give an Oil (non-aqueous) Phase Mixture Part C;

(e) emulsifying a mixture of Aqueous Phase Mixture Part A and the Oil (non-aqueous) Phase Mixture Part C at about 70–80° C.; and (f) cooling to room temperature.

If necessary, the pH of the pharmaceutical composition is adjusted with either aqueous sodium hydroxide or hydrochloric acid to give a pH of about 5.0 to about 7.0, more preferably, about 5.5 to about 6.5.

The invention also relates to a pharmaceutical composition obtained by the process of the invention.

Optionally, the pharmaceutical compositions of the present invention may contain additional ingredients including antimicrobials, excipients, dyes, perfumes, fragrances, preservatives, anti-oxidants, opacifiers, thickening agents, preservatives, stabilizers and the like. Such materials, when added, should not unduly interfere with the activity of the pharmaceutically active agent nor possess irritating properties. Such formula modifications to improve cosmetic acceptability are well within the skill in the art.

The pharmaceutical composition of the invention may be provided in a jar, tube or other suitable container as is well known in the art.

The invention also relates to a method of treating the inflammatory and pruritic manifestations of corticosteroid-responsive dermatoses in an animal in need thereof, comprising administering topically an effective amount of a pharmaceutical composition of the invention to said animal. Preferably, the animal is a mammal, more preferably, a human. Preferably, the dermatosis is psoriasis, seborrheic dermatitis, atopic dermatitis, contact dermatitis, eczema or any skin condition characterized by dermal and inflammatory pruritis.

The individual dosage is determined according to the particular condition being treated The compositions may be applied from one to six times daily or otherwise as is necessary to treat the skin condition. If the pharmaceutically active agent is a corticosteroid, then the composition is preferably applied one to four times daily, more preferably, once or twice daily. In the most preferred application, the corticosteroid-containing composition is applied as a thin layer to the affected area twice daily and rubbed into the skin completely.

Any animal which will benefit from the pharmaceutical composition of the invention is within the scope of animals that may be treated according to the present invention. Such animals include humans and veterinary animals.

Having now generally described the invention, the same will be more readily understood through reference to the following examples which are provided by way of illustration, and are not intended to be limiting of the present invention, unless specified. For example, the times, temperatures and amounts of ingredients may be modified using routine experimentation.

EXAMPLE 1

Preparation of a Cream Formulation of Triamcinolone Acetonide Containing Substantial Amounts of $C_{16}$ and $C_{18}$ n-Alcohols General STEP 1: Inspect processing rooms and equipment listed to insure they are clean and ready for use.

STEP 2: Pre-weigh each ingredient listed on the weigh-up sheet (manufacturing record) into a clean container.

Part A: Aqueous Phase

STEP 3: Add the appropriate amount of purified water USP, to a clean stainless steel steam-jacketed mixing kettle equipped with a turbine mixer and scraper blade mixer. Begin mixing and heat the water to 70–80° C. Maintain at 70–80° C. through Step 12 (cooling emulsion).

STEP 4: Add propylene glycol USP. Cover the mixing kettle and mix until the propylene glycol dissolves. Mix for at least 5 minutes.

STEP 5: Add sodium lauryl sulfate NF. Cover the mixing kettle and mix on low speed until the sodium lauryl sulfate powder dissolves. Continue mixing at low speed.

Part B: Triamcinolone Acetonide/Laurocapram Premix

STEP 6: Add laurocapram (AZONE®) to a clean stainless steel mixing vessel equipped with an appropriate mixer. Cover the mixing vessel and heat, using an appropriate heater, the AZONE® to 70–80° C. while stirring at low speed. Maintain the temperature 70–80° C. through Step 12.

STEP 7: Add triamcinolone acetonide USP. Cover the mixing vessel and mix until triamcinolone acetonide dissolves. Continue mixing at low speed.

Part C. Oil (non-aqueous) Phase

STEP 8: Add glyceryl monostearate (preferably, CERASYNT® SD from Van Dyk & Co., Inc.), cetyl alcohol NF and stearyl alcohol NF, to a clean stainless steel steam-jacketed mixing kettle equipped with an appropriate mixer. Cover the kettle and heat the oil phase to 70–80° C. As the materials begin to melt, begin stirring at low speed, Maintain the temperature at 70–80° C. through Step 12.

STEP 9: Add Part B: triamcinolone acetonide/laurocapram premix (from step 7) to Part C: oil (non-aqueous) phase (from Step 8). Cover the mixing kettle and mix until thoroughly blended. Continue mixing on low speed.

Emulsification

STEP 10: Increase the speed of the mixer for Part A, the aqueous phase in Step 5, to high. Slowly add combined Parts B and C (from Step 9) to Part A (Step 5). Cover and continue to mix.

STEP 11: Turn off the steam, drain the steam jacket, and continue mixing.

STEP 12: Rinse the kettle used in Step 9 with a appropriate amount of purified water USP, and add the rinse solution to Step 10.

STEP 13: Cover and continue mixing using a propeller and side sweep. Cool the batch to 55–60° C., using cooling water in the jacket if necessary.

STEP 14: Check and record the pH of a 1:10 mixture in purified water, USP.

STEP 15: Process the emulsion from Step 13 through the homogenizer using two medium and one fine generator. Continue homogenizing the emulsion for at least 45 minutes.

STEP 16: Pump the product through the homogenizer into poly-lined plastic drums.

STEP 17: Take beginning, middle and end samples during the pumping operation for bulk drug product.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications, patents and patent applications mentioned in this specification are indicative of the level of skill of those in the art to which the invention pertains. All publications, patents and patent applications are herein incorporated by reference to the same extent as if each individual publication or patent application was specifically and individually indicated to be incorporated by reference in their entirety.

What is claimed is:

1. A pharmaceutical composition for topical administration, comprising:
   (a) a safe and pharmaceutically effective amount of a pharmaceutically active agent;
   (b) about 15–97% by weight of a diol selected from the group consisting of 1,2-propanediol, 1,2-butanediol, 1,3-butanediol, 2,3-butanediol, and mixtures thereof;
   (c) about 0.5–25% by weight of cetyl alcohol;
   (d) about 0.1–25% by weight of glyceryl monostearate;
   (e) about 0.9–5.0% by weight of laurocapram;
   (f) about 0.5–25% by weight of stearyl alcohol;
   (g) about 0.01–1.0% by weight of sodium lauryl sulfate; and
   (h) water.

2. The pharmaceutical composition of claim 1, which comprises:

| Ingredients | Percent (% w/w) (about) |
| --- | --- |
| Corticosteroid | 0.05 |
| Propylene Glycol | 15.00 |
| Cetyl Alcohol | 8.00 |
| Glyceryl Monostearate | 3.50 |
| Laurocapram | 1.60 |
| Stearyl Alcohol | 1.00 |
| Sodium Lauryl Sulfate | 0.10 |
| Purified Water | QS ad 100%. |

3. The pharmaceutical composition of claim 1, which consists essentially of:

| Ingredients | Percent (% w/w) |
| --- | --- |
| Triamcinolone acetonide, USP | 0.05 |
| Propylene Glycol, USP | 15.00 |
| Cetyl Alcohol, NF | 8.00 |
| Glyceryl Monostearate | 3.50 |
| Laurocapram | 1.60 |
| Stearyl Alcohol, NF | 1.00 |
| Sodium Lauryl Sulfate, NF (Powder) | 0.10 |
| Purified Water, USP | QS ad 100%. |

4. A process for preparing a topical pharmaceutical composition, comprising:

(a) admixing water, a diol and sodium lauryl sulfate at about 70–80° C. at least until the diol and sodium lauryl sulfate dissolves to give an Aqueous Phase Mixture Part A, wherein said diol is selected from the group consisting of 1,2-propanediol, 1,2-butanediol, 1,3-butanediol, 2,3-butanediol, and mixtures thereof;

(b) admixing laurocapram and a pharmaceutically active agent at about 70–80° C. at least until the corticosteroid dissolves to give a Agent/Laurocapram Premix Part B;

(c) admixing glyceryl monostearate, cetyl alcohol and stearyl alcohol at about 70–80° C. until at least the admixture melts;

(d) admixing with said melted admixture said Agent/Laurocapram Premix Part B at about 70–80° C. and mixing at least until thoroughly blended to give an Oil (non-aqueous) Phase Mixture Part C;

(e) emulsifying a mixture of Aqueous Phase Mixture Part A and the Oil (non-aqueous) Phase Mixture Part C at about 70–80° C.; and (f) cooling to room temperature.

5. The process of claim 4, wherein said pharmaceutically active agent is a corticosteroid.

6. The process of claim 5, wherein said corticosteroid is triamcinolone acetonide.

7. The process of claim 4, wherein said pharmaceutical composition comprises:
   (a) a pharmaceutically effective amount of said pharmaceutically active agent;
   (b) about 15–97% by weight of said diol;
   (c) about 0.5–25% by weight of cetyl alcohol;
   (d) about 0.1–25% by weight of glyceryl monostearate;
   (e) about 0.9–5.0% by weight of laurocapram;
   (f) about 0.5–25% by weight of stearyl alcohol;
   (g) about 0.01–1.0% by weight of sodium lauryl sulfate; and
   (h) water.

8. The process of claim 4, wherein said pharmaceutical composition comprises:

| Ingredients | Percent (% w/w) (about) |
| --- | --- |
| Corticosteroid | 0.05 |
| Propylene Glycol | 15.00 |
| Cetyl Alcohol | 8.00 |
| Glyceryl Monostearate | 3.50 |
| Laurocapram | 1.60 |
| Stearyl Alcohol | 1.00 |
| Sodium Lauryl Sulfate | 0.10 |
| Purified Water | QS ad 100%. |

9. The process of claim 4, wherein said pharmaceutical composition consists essentially of:

| Ingredients | Percent (% w/w) |
| --- | --- |
| Triamcinolone Acetonide, USP | 0.05 |
| Propylene Glycol, USP | 15.00 |
| Cetyl Alcohol, NF | 8.00 |
| Glyceryl Monostearate | 3.50 |
| Laurocapram | 1.60 |
| Stearyl Alcohol, NF | 1.00 |

| Ingredients | Percent (% w/w) |
|---|---|
| Sodium Lauryl Sulfate, NF (Powder) | 0.10 |
| Purified Water, USP | QS ad 100%. |

10. A pharmaceutical composition obtained by the process of claim 4.

11. The pharmaceutical composition of claim 10, which comprises:
   (a) a pharmaceutically effective amount of said pharmaceutically active agent;
   (b) about 15–97% by weight of said diol;
   (c) about 0.5–25% by weight of cetyl alcohol;
   (d) about 0.1–25% by weight of glyceryl monostearate;
   (e) about 0.9–5.0% by weight of laurocapram;
   (f) about 0.5–25% by weight of stearyl alcohol;
   (g) about 0.01–1.0% by weight of sodium lauryl sulfate; and
   (h) water.

12. The pharmaceutical composition of claim 10, which comprises:

| Ingredients | Percent (% w/w) (about) |
|---|---|
| Corticosteroid | 0.05 |
| Propylene Glycol | 15.00 |
| Cetyl Alcohol | 8.00 |
| Glyceryl Monostearate | 3.50 |
| Laurocapram | 1.60 |
| Stearyl Alcohol | 1.00 |
| Sodium Lauryl Sulfate | 0.10 |
| Purified Water | QS ad 100%. |

13. The pharmaceutical composition of claim 10, which consists essentially of:

| Ingredients | Percent (% w/w) |
|---|---|
| Triamcinolone Acetonide, USP | 0.05 |
| Propylene Glycol, USP | 15.00 |
| Cetyl Alcohol, NF | 8.00 |
| Glyceryl Monostearate | 3.50 |
| Laurocapram | 1.60 |
| Stearyl Alcohol, NF | 1.00 |
| Sodium Lauryl Sulfate, NF (Powder) | 0.10 |
| Purified Water, USP | QS ad 100%. |

14. A method of treating an inflammatory skin condition in an animal in need thereof, comprising administering an amount of said pharmaceutical composition of claim 1 or 10 to said animal effective to treat said inflammatory skin condition.

15. The method of claim 14, wherein said inflammatory skin condition is psoriasis, seborrheic dermatitis, atopic dermatitis, contact dermatitis or eczema.

16. The method of claim 14, wherein said pharmaceutical composition comprises:
   (a) an amount of said pharmaceutically active corticosteroid effective to treat said inflammatory skin condition;
   (b) about 15–97% by weight of said diol;
   (c) about 0.5–25% by weight of cetyl alcohol;
   (d) about 0.1–25% by weight of glyceryl monostearate;
   (e) about 0.9–5.0% by weight of laurocapram;
   (f) about 0.5–25% by weight of stearyl alcohol;
   (g) about 0.01–1.0% by weight of sodium lauryl sulfate; and
   (h) water.

17. The method of claim 14, wherein said pharmaceutical composition comprises:

| Ingredients | Percent (% w/w) (about) |
|---|---|
| Corticosteroid | 0.05 |
| Propylene Glycol | 15.00 |
| Cetyl Alcohol | 8.00 |
| Glyceryl Monostearate | 3.50 |
| Laurocapram | 1.60 |
| Stearyl Alcohol | 1.00 |
| Sodium Lauryl Sulfate | 0.10 |
| Purified Water | QS ad 100%. |

18. The method of claim 14, wherein said pharmaceutical composition consists essentially of:

| Ingredients | Percent (% w/w) |
|---|---|
| Triamcinolone Acetonide, USP | 0.05 |
| Propylene Glycol, USP | 15.00 |
| Cetyl Alcohol, NF | 8.00 |
| Glyceryl Monostearate | 3.50 |
| Laurocapram | 1.60 |
| Stearyl Alcohol, NF | 1.00 |
| Sodium Lauryl Sulfate, NF (Powder) | 0.10 |
| Purified Water, USP | QS ad 100%. |

* * * * *

UNITED STATES PATENT AND TRADEMARK OFFICE
CERTIFICATE OF CORRECTION

PATENT NO. : 6,271,219 B1  
DATED : August 7, 2001  
INVENTOR(S) : Vaidyanathan et al.

Page 1 of 1

It is certified that error appears in the above-identified patent and that said Letters Patent is hereby corrected as shown below:

Title page,  
Delete Donald J. Gerhart from the inventive entity.

Signed and Sealed this

Fifteenth Day of January, 2002

*Attest:*

JAMES E. ROGAN  
*Attesting Officer*   *Director of the United States Patent and Trademark Office*